(12) United States Patent
Kim et al.

(10) Patent No.: US 10,422,752 B2
(45) Date of Patent: Sep. 24, 2019

(54) SUBSTRATE FOR SURFACED ENHANCED RAMAN SCATTERING, FABRICATION METHOD FOR THE SAME AND ANALYZING METHOD USING THE SAME

(71) Applicant: KOREA INSTITUTE OF MACHINERY & MATERIALS, Daejeon (KR)

(72) Inventors: Dong Ho Kim, Gyeongsangnam-do (KR); Sung Gyu Park, Gyeongsangnam-do (KR); Chang Su Kim, Gyeongsangnam-do (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 0 days.

(21) Appl. No.: 14/947,960

(22) Filed: Nov. 20, 2015

(65) Prior Publication Data
US 2016/0146737 A1    May 26, 2016

(30) Foreign Application Priority Data
Nov. 21, 2014 (KR) .......... 10-2014-0163737

(51) Int. Cl.
*B82Y 15/00* (2011.01)
*G01N 21/65* (2006.01)
(Continued)

(52) U.S. Cl.
CPC ............ *G01N 21/658* (2013.01); *B82Y 15/00* (2013.01); *B82Y 20/00* (2013.01); *B82Y 30/00* (2013.01)

(58) Field of Classification Search
CPC .... G01N 21/658; G01N 21/554; B82Y 15/00; B82Y 40/00; B22F 1/0044
See application file for complete search history.

(56) References Cited

U.S. PATENT DOCUMENTS

2008/0003576 A1* 1/2008 Zhang .................. C12Q 1/6816
435/6.11
2008/0251381 A1* 10/2008 Shibata .................. C25D 13/02
204/483
(Continued)

FOREIGN PATENT DOCUMENTS

KR    1010738530000    10/2011
WO    WO 2014/022330 A2 *    6/2014

OTHER PUBLICATIONS

Liu, Jian-Wei et al. "Ordering Ag nanowire arrays by a glass capillary: A portable, reusable and durable SERS substrate." www.nature.com/scientificreports. Scientific Reports. vol. 2:987. DOI: 10.1038/srep00987. pp. 1-7. Dec. 17, 2012.
(Continued)

*Primary Examiner* — Maurice C Smith
(74) *Attorney, Agent, or Firm* — Moore & Van Allen PLLC; Henry B. Ward, III (57) ABSTRACT

The present disclosure relates to a substrate for surface enhanced Raman scattering, a fabricating method for the same and an analyzing method using the same. The present disclosure may provide a substrate for surface enhanced Raman scattering having excellent surface enhanced Raman scattering effects by randomly stacking of Ag nanowires in a simple way by utilizing a substrate having a filtering function, and a method for efficiently analyzing a material to be analyzed using the same.

17 Claims, 8 Drawing Sheets
(4 of 8 Drawing Sheet(s) Filed in Color)

(51) Int. Cl.
*B82Y 30/00* (2011.01)
*B82Y 20/00* (2011.01)

(56) References Cited

U.S. PATENT DOCUMENTS

| | | | | |
|---|---|---|---|---|
| 2009/0225310 | A1* | 9/2009 | Yang | G01N 21/658 |
| | | | | 356/301 |
| 2012/0224255 | A1* | 9/2012 | Bora | B82Y 20/00 |
| | | | | 359/346 |
| 2012/0273662 | A1* | 11/2012 | Caldwell | G01N 21/658 |
| | | | | 250/214.1 |
| 2012/0300203 | A1 | 11/2012 | Tyagi et al. | |
| 2014/0356411 | A1* | 12/2014 | Fan | G01N 21/658 |
| | | | | 424/443 |

OTHER PUBLICATIONS

Chen, Miaosi et al. "Layer-By-Layer Assembly of Ag Nanowires into 3D Woodpile-like Structures to Achieve High Dernsity "Hot Spots" for Surface-Enhanced Raman Scattering." Langmuir. www.pubs.acs.org/Langmuir. ACS Publications. © 2013 American Chemical Society. Dx.doi.org/10.1021/la4012108. Langmuir 2013, vol. 29, pp. 7061-7069.

* cited by examiner

SUBSTRATE FOR SURFACED ENHANCED RAMAN SCATTERING, FABRICATION METHOD FOR THE SAME AND ANALYZING METHOD USING THE SAME

CROSS REFERENCE TO RELATED APPLICATION

This application claims the benefit of Korean Patent Application No. 10-2014-0163737, filed on Nov. 21, 2014 in the Korean Intellectual Property Office, the entire disclosure of which is incorporated herein by reference for all purposes.

TECHNICAL FIELD

The present disclosure relates to a substrate for surface enhanced Raman scattering, a fabricating method for the same and an analyzing method using the same.

BACKGROUND

Raman scattering or the Raman Effect is an inelastic photon scattering phenomenon. When photons are scattered from an atom or molecule, most photons are elastically scattered (Rayleigh scattering), such that the scattered photons have the same energy (frequency and wavelength) as the incident photons. A small fraction of the scattered photons (approximately 1 in 10 million) are scattered by an excitation, with the scattered photons having a frequency different from, and usually lower than, that of the incident photons. In a gas, Raman scattering can occur with a change in energy of a molecule due to a transition to another (usually higher) energy level.

Raman Effect (Raman shift) is exhibited in almost organic molecules including not only by polar molecules but also by non-polar molecules which have induction polarizability when Raman spectroscopy using Raman scattering is applied. It is thus more suitable for the detection of biomolecules such as proteins, genes and the like since it is not affected by interference caused by water molecules.

On the other hand, specific wavelengths of Raman emission spectrum represents chemical composition and structure features so that it can be used to directly analyze materials using Raman signals.

Surface enhanced Raman scattering is associated with surface plasmon resonance phenomena caused with excitation by electromagnetic radiation. Signal intensities are greatly amplified with the electromagnetic resonance.

It has been studied in a variety of structures for inducing this surface enhanced Raman scattering, and recently technologies relating to substrates for surface enhanced Raman scattering are being developed with utilization metal nanoparticles or metal nanowires.

Ag nanowire arrays by a glass capillary: A portable, reusable and durable SERS substrate in Scientific Reports 2, Article number: 987, doi: 10.1038/srep00987 discloses a technique for aligning Ag nanowires along the direction of a capillary on the inner wall of the capillary.

Assembly of Ag Nanowires into 3D Woodpile-like Structures to Achieve High Density Spots for Surface-Enhanced Raman Scattering in Langmuir, 2013, 29 (23), pp 7061-7069, DOI: 10.1021/la4012108 discloses a method for alternatively laminating Ag nanowires according to the Langmuir-Blodgett method.

KR Patent No. 10-1073853 discloses a manufacturing method of a nano structured net-shaped film on a substrate. It teaches a method for forming the nano structure by a filtration method. However, it requires a transcription process after filtration and does not teach its application as a substrate for surface enhanced Raman scattering. It discloses that the nano substrate is a carbon nanotube which is manufactured by transcription of a membrane in which the nano structure net-shaped film is formed on the substrate such as a silicon oxide and then separating the membrane using surface tension difference between the membrane and the substrate (FIG. 1). Thus, its technical field is different from a substrate for surface enhanced Raman scattering of the present disclosure.

US Patent Publication No. 2012-0300203 discloses a method for the formation of a substrate with filtering capabilities by utilizing a nanoparticle ink. This teaches that nanoparticles with much smaller size than a fiber strand are densely adhered on a fiber strand which is a part of the substrate with filtering capabilities.

The present disclosure is to provide a substrate for surface enhanced Raman scattering which is prepared by using filtering functions and is able to suitable for Raman signal analyses, a fabricating method for the same and an analyzing method using the same.

SUMMARY

This summary is provided to introduce a surface enhanced Raman scattering having excellent surface enhanced Raman scattering (SERS) effects using a substrate with filtering capabilities, a fabricating method for the same and an analyzing method using the same. This Summary is not intended to identify key features or essential features of the claimed subject matter, nor is it intended to be used as an aid in determining the scope of the claimed subject matter.

In one general aspect, there is provided a substrate for surface enhanced Raman scattering including: a substrate including a plurality of pores; and metal-containing nanowires configured not to pass through the pores and to be aggregated on the substrate, wherein the metal-containing nanowires form nanogaps configured to induce surface plasmon resonance with adjacent metal-containing nanowires.

In another general aspect, there is provided a Raman scattering apparatus including the substrate for surface enhanced Raman scattering of the present disclosure described above.

In still another general aspect, there is provided a method for fabricating the substrate for surface enhanced Raman scattering of the present disclosure. The method may include preparing a substrate including a plurality of pores; filtering a solution including metal-containing nanowires to aggregate the metal-containing nanowires on the substrate; and drying the substrate, wherein the metal-containing nanowires do not pass the pores and form nanogaps configured to induce surface plasmon resonance with adjacent metal-containing nanowires.

In still another general aspect, there is provided an analyzing method using a substrate for surface enhanced Raman scattering, the analyzing method including preparing a substrate for surface enhanced Raman scattering of the present disclosure; forming a mixed solution by mixing a material to be analyzed to a solution including metal-containing nanowires; filtrating the mixed solution to the substrate; drying the substrate; and detecting a Raman signal by light irradiation into the material to be analyzed, wherein the metal-containing nanowires do not pass the pores and form nanogaps configured to induce surface plasmon resonance with adjacent metal-containing nanowires.

In still another general aspect, there is provided an analyzing method using a substrate for surface enhanced Raman scattering, the analyzing method including preparing a substrate for surface enhanced Raman scattering of the present disclosure; filtrating a material to be analyzed to the substrate; and detecting a Raman signal by light irradiation into the material to be analyzed.

The present disclosure may provide a substrate for surface enhanced Raman scattering having excellent surface enhanced Raman scattering effects in a simple way by utilizing a substrate having a filtering function and a method for efficiently analyzing a material to be analyzed using the same.

Other features and aspects will be apparent from the following detailed description, the drawings, and the claims.

BRIEF DESCRIPTION OF DRAWINGS

Color Photographs

The patent or application file contains at least one photograph executed in color. Copies of the patent or patent application publication with color photographs(s) will be provided by the Office upon request and payment of the necessary fee.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The terms used in the description are intended to describe certain embodiments only, and shall by no means restrict the present disclosure. Unless clearly used otherwise, expressions in the singular number include a plural meaning. In the present description, an expression such as "comprising" or "consisting of" is intended to designate a characteristic, a number, a step, an operation, an element, a part or combinations thereof, and shall not be construed to preclude any presence or possibility of one or more other characteristics, numbers, steps, operations, elements, parts or combinations thereof.

Hereinafter, certain embodiments of the present disclosure will be described in detail with reference to the accompanying drawings. Identical or corresponding elements will be given the same reference numerals, regardless of the figure number, and any redundant description of the identical or corresponding elements will not be repeated.

Figure 1A:
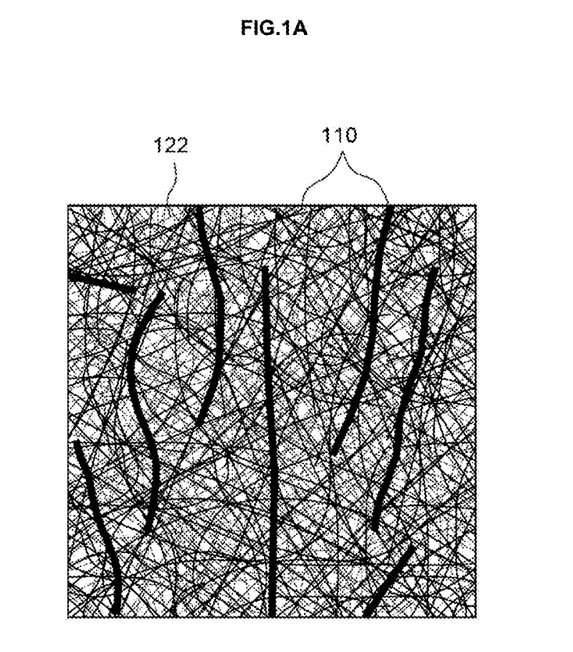
FIG. 1A illustrates an example of a substrate for surface enhanced Raman scattering and an example of a part of its fabrication process.
Figure 1B:
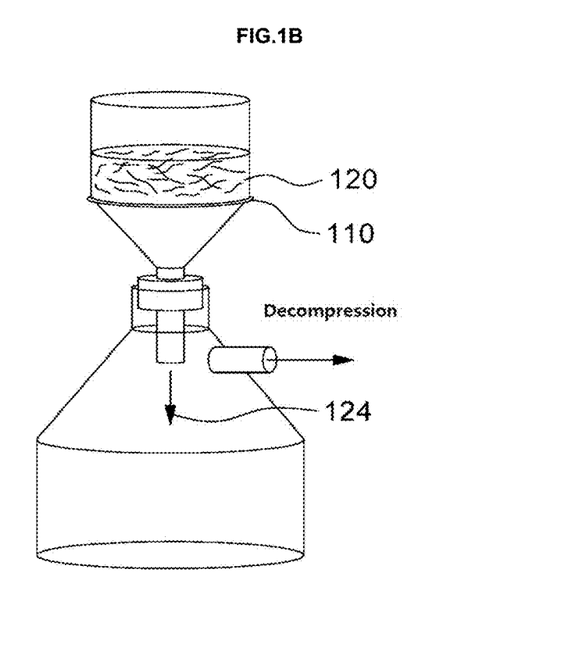
FIG. 1B illustrates an example of a part of the fabrication process for a substrate for surface enhanced Raman scattering.

FIGS. 1A and 1B illustrate an example of a substrate for surface enhanced Raman scattering and an example of a part of its fabrication process.

Referring to FIG. 1A, a substrate for surface enhanced Raman scattering includes substrates 110 and metal-containing nanowires 122. The substrates 110 are represented by the thickest lines and medium thick lines, and the metal-containing nanowires 122 are represented by the thin lines.

The substrate 110 may include a plurality of pores so that a solution 120 is filtered therethrough. When the solution 120 including the metal-containing nanowires 122 is filtered through the substrate 110, materials, except the metal-containing nanowires 122, which are the solution including a stabilizer may be filtered through the plurality of pores in the substrate 110.

The substrate 110 may be one chosen from glass fiber, alumina, Teflon (polytetrafluoroethylene, PTFE), polycarbonate (PC), cellulose and paper, but it is not limited thereto. The substrate 110 may be any substrate having filtering capabilities regardless of material.

A glass fiber filter is used as an example of the substrate 110. The glass fiber has advantages of allowing various organic solvents to be used, not large signal noises and low cost, etc.

When any process including a drying process such as heat treatment is performed to the substrate for surface enhanced Raman scattering, heat resistance may be needed to withstand high temperatures. The heat resistance is needed since temperature of gas or solution to be analyzed may be high when a Raman signal is analyzed or it may need ability to withstand high temperatures during analysis. When the glass fiber is used as an example of the substrate 110 in the present disclosure, a substrate for surface enhanced Raman scattering having excellent heat resistance under such conditions can be manufactured.

The metal-containing nanowires 122 may have an enough length not to pass through the pores.

The metal-containing nanowires 122 may be aggregated in irregular directions on the substrate 110 to form a plurality of cross points (junctions).

Since hot spots at which plasmon resonance occurs are formed near the cross points, they may contribute Raman signal enhancement with light irradiation.

The metal-containing nanowires 122 aggregated on the substrate 110 may be formed by vacuum filtering the solution 120 including the metal-containing nanowires 122 such as nanowire ink on the substrate 110. Since the metal-containing nanowires 122 have an enough length not enough to pass through the pores of the substrate 110, most of them may not pass the substrate 110 with vacuum filtration and thus be aggregated on the substrate 110.

Size and density of the metal-containing nanowires 122 may be adjusted to form nanogaps which induce the surface plasmon resonance with adjacent metal-containing nanowires 122.

The density of the metal-containing nanowires 122 may be adjusted by utilizing various factors, for example a concentration of the metal-containing nanowires 122 in the solution 120 and filtration volume of the solution 120.

Aggregation of the metal-containing nanowires 122 means thickly formed and laminated metal-containing nanowires 122 on the substrate 110.

A thickness of the metal-containing nanowires 122 to be aggregated may be adjusted using a concentration of the metal-containing nanowires 122 in the solution 120 and filtration volume of the solution 120.

FIG. 1B illustrates a vacuum filtration apparatus.

The solution 120 including the metal-containing nanowires 122 is filtered through the substrate 110 and filtrate 124 is collected in a container. The metal-containing nanowires 122 are aggregated on the substrate 110 since they cannot pass through the substrate 110.

The filtrate 124 may include a coating material such as polyvinylpyrrolidone (PVP) which is used for dispersion stability of the metal-containing nanowires 122. The coating material may be removed using heat treatment or may be used for controlling the nanogaps. For example, when the density of the metal-containing nanowires 122 increases, the nanogaps are gradually reduced and the metal-containing nanowires 122 become thus in contact with each other and the nanogaps are eventually disappeared. Thus, when the coating material is not removed, the nanogaps may be present in minimized sizes.

The coating material may cause noises when a Raman signal is analyzed using the substrate for surface enhanced Raman scattering. In this case, after gaps between the metal-containing nanowires are formed using the coating material, the coating material is removed and then a material to be analyzed is adsorbed to perform Raman signal analysis.

In an embodiment of the present disclosure, most of the metal-containing nanowires 122 do not pass through the substrate 110 and are thus aggregated thereon due to their enough length. The metal-containing nanowires 122 aggregated on the substrate 110 may form numerous cross points which become hot spots since nanogaps are formed around the cross points.

The hot spots may be formed vertically or horizontally. As the metal-containing nanowires 122 are laminated thicker and thicker, Raman intensity may be enhanced. However, the Raman intensity is not enhanced further from a certain thickness or above. In this description, it is referred to as the thickness where the Raman signal enhancement is saturated. When the thickness where the Raman signal does not enhance is known in advance, it may be utilized in the fabrication process. For example, the thickness where the Raman signal does not enhance is recorded and determined and the thickness of the metal-containing nanowires 122 to be aggregated may be then determined based thereon. In this case, laser focal length dependency becomes lowered during analysis using Raman signals.

Since each of the metal-containing nanowires 122 has irregularly its own orientation instead of a particular orientation, there is little outcome difference associated with laser orientation.

Figure 2:
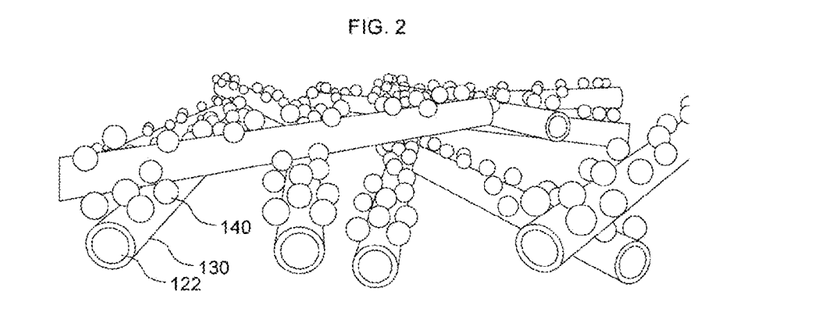
FIG. 2 illustrates an example of a substrate for surface enhanced Raman scattering.

FIG. 2 illustrates an example of a substrate for surface enhanced Raman scattering.

The structure in FIG. 2 is to illustrate for improvement of the surface enhanced effect compared to the structure in FIG. 1.

Referring to FIG. 2, the substrate for surface enhanced Raman scattering further includes an insulating film 130 and metal-containing nanoparticles 140. The structure of the substrate 110 is omitted in FIG. 2 for brief description.

The insulating film 130 may be formed on the metal-containing nanowires 122. The insulating film 130 may be formed between the metal-containing nanowires 122 and the metal-containing nanoparticles 140 to form nanogaps therebetween.

The insulating film 130 may be formed of any one chosen from alumina, metal oxide, metal sulfide, metal halide, silica, zirconium oxide and iron oxide, but it is not limited thereto.

The metal-containing nanoparticles 140 may be formed on the insulating film 130 and be spaced apart with each other. The metal-containing nanoparticles 140 may form nanogaps to induce surface plasmon resonance.

The spaced-apart distance of the metal-containing nanoparticles 140 may be adjusted during the manufacturing process to form nanogaps.

The nanogaps may be formed at least one area chosen from between the metal-containing nanowires 122, between the metal-containing nanowires 122 and the metal-containing nanoparticles 140, and between the metal-containing nanoparticles 140.

Two types of nanogaps may be formed between the metal-containing nanowires 122 of which one is formed due to irregular distance between the metal-containing nanowires 122 having irregular orientation and the other is formed around cross points which are formed when the metal-containing nanowires 122 having irregular orientation are aggregated.

The nanogaps between the metal-containing nanowires 122 and the metal-containing nanoparticles 140 are formed naturally due to the present of the insulating film 130. Plasmon resonance properties such as wavelength of the plasmon resonance may be controlled by controlling the thickness of the insulating film 130.

The metal-containing nanoparticles 140 are formed to be spaced apart with each other on the insulating film 130 so that nanogaps may be formed between the metal-containing nanoparticles 140 and the adjacent metal-containing nanoparticles 140.

As described above, the nanogaps can be formed at various areas in the substrate for surface enhanced Raman scattering so that intensity and uniformity may be improved with increased density of hot spots during light irradiation.

When a material is analyzed using the substrate for surface enhanced Raman scattering of the present disclosure, the material may be adsorbed to the nanogaps so that large-scaled material with a low concentration can be analyzed.

The metal in the metal-containing nanowires 122 or in the metal-containing nanoparticles 140 may be any one chosen from Ag, Al, Au, Co, Cu, Fe, Li, Ni, Pd, Pt, Rh, Ru and an alloy thereof, but it is not limited thereto.

FIGS. 3A, 3B, 3C and 3D illustrate an example of metal-containing nanowires aggregated on a substrate for surface enhanced Raman scattering at different magnifications.

Figure 3A:
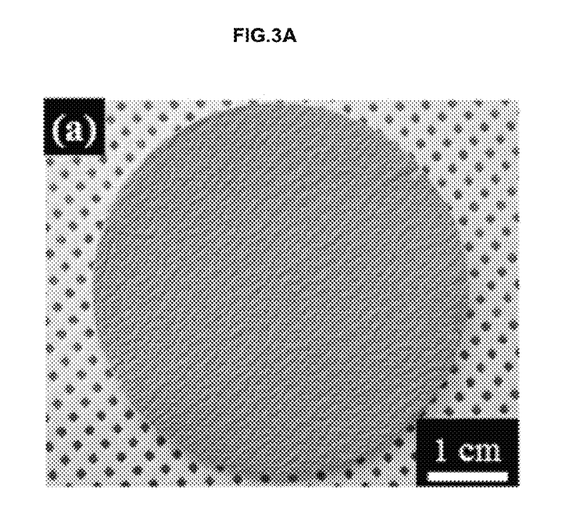
FIG. 3A illustrates an example of metal-containing nanowires aggregated on a substrate for surface enhanced Raman scattering.
Figure 3B:
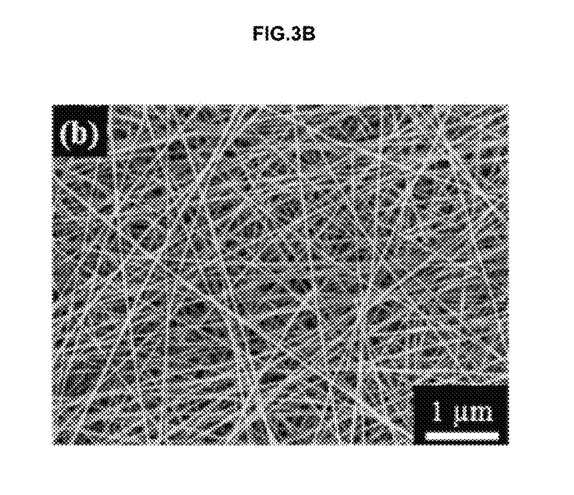
FIG. 3B illustrates the example of metal-containing nanowires aggregated on a substrate for surface enhanced Raman scattering of FIG. 3A at a higher magnification.
Figure 3C:
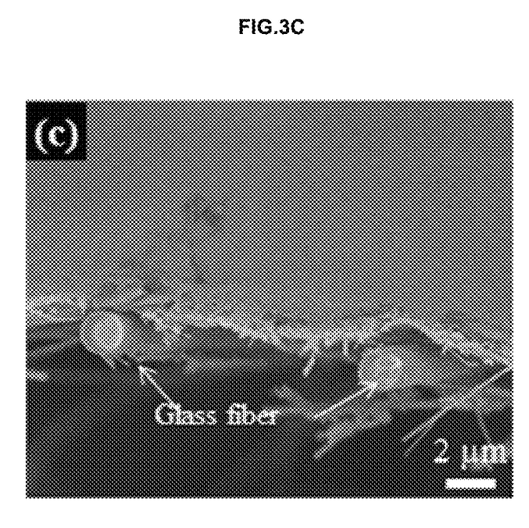
FIG. 3C illustrates the example of metal-containing nanowires aggregated on a substrate for surface enhanced Raman scattering of FIG. 3A at a higher magnification.
Figure 3D:
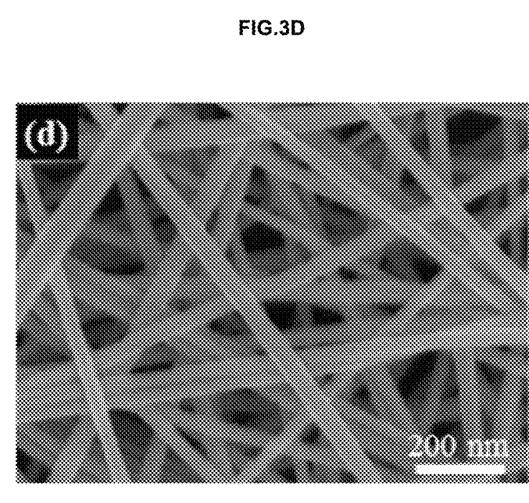
FIG. 3D illustrates the example of metal-containing nanowires aggregated on a substrate for surface enhanced Raman scattering of FIG. 3A at a higher magnification.

FIG. 3A illustrates the metal-containing nanowires 122 aggregated on the substrate 110, FIG. 3B and FIG. 3C are a top view and a side view of the metal-containing nanowires 122 aggregated on the substrate 100, respectively, and FIG. 3D is a SEM image of the metal-containing nanowires 122.

Referring to FIG. 3A, it is noted that the metal-containing nanowires 122 are uniformly distributed on the substrate with a diameter of 48 mm.

As also shown in FIG. 3B and FIG. 3C, since the pore size of the substrate 110 is less than the length of the metal-containing nanowires 122, most of the metal-containing nanowires 122 do not pass through the substrate 110 and are aggregated on the substrate 110. Only other materials, except the metal-containing nanowires 122, are filtered with vacuum filtration which allows for the metal-containing nanowires 122 to be aggregated closely and densely.

Referring to FIG. 3D, the metal-containing nanowires 122 are arranged irregularly to form numerous cross points near which hot spots are formed. It is also noted that the metal-containing nanowires 122 are laminated in multiple layers.

A 0.7 μm-sized glass fiber filter is used as an example of the substrate 110 and nanowire ink including Ag nanowires with a diameter of about 40 nm and a length of about 50 μm is used. Ag nanowires are aggregated on the substrate 110 with vacuum filtration.

When a material is analyzed using the substrate for surface enhanced Raman scattering of the present disclosure, the material may be adsorbed to the nanogaps so that large-scaled material with a low concentration can be analyzed.

FIGS. 4A, 4B, 4C, and 4D illustrate examples of metal-containing nanowires 122 having different sizes of nanoparticles deposited on a substrate for surface enhanced Raman scattering.

Figure 4A:
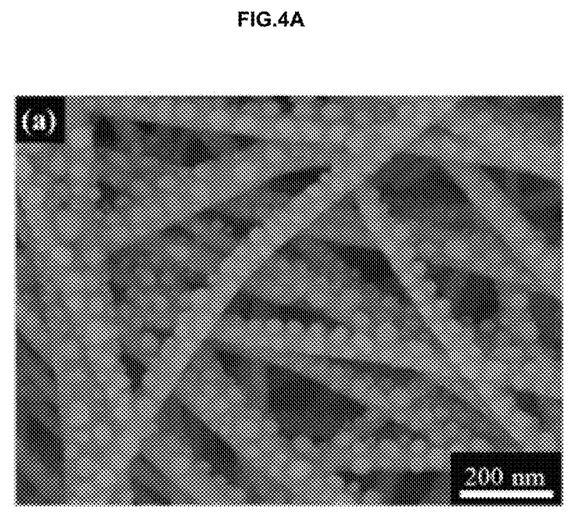
FIG. 4A illustrates another example of metal-containing nanowires 122 having different sizes of nanoparticles deposited on a substrate for surface enhanced Raman scattering.
Figure 4B:
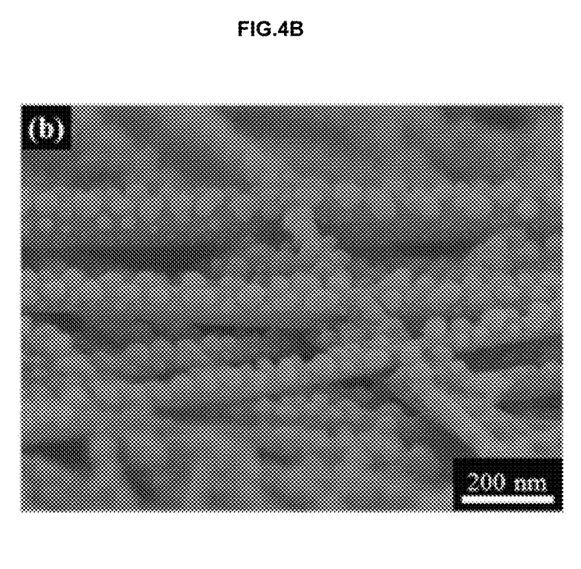
FIG. 4B illustrates another example of metal-containing nanowires 122 having different sizes of nanoparticles deposited on a substrate for surface enhanced Raman scattering.
Figure 4C:
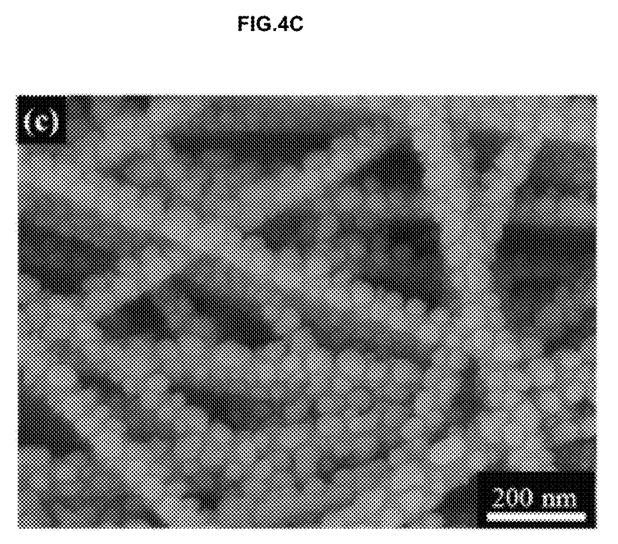
FIG. 4C illustrates another example of metal-containing nanowires 122 having different sizes of nanoparticles deposited on a substrate for surface enhanced Raman scattering.
Figure 4D:
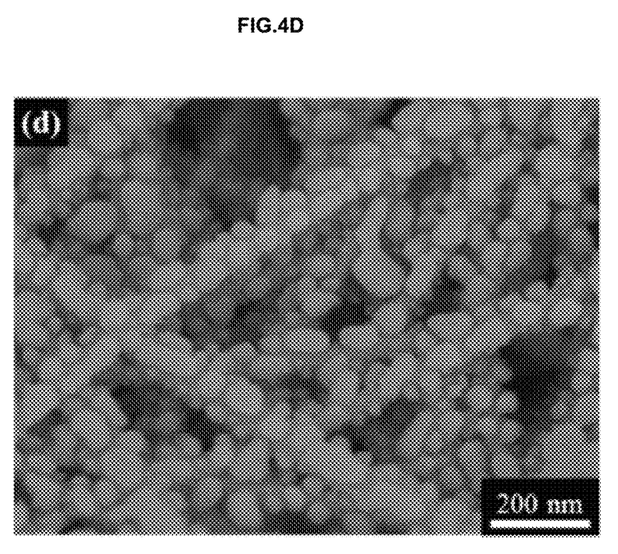
FIG. 4D illustrates another example of metal-containing nanowires 122 having different sizes of nanoparticles deposited on a substrate for surface enhanced Raman scattering.

FIG. 4A illustrates the metal-containing nanoparticles 140 which are deposited in a thickness of 9 nm with Ag, and FIGS. 4B, 4C and 4D illustrate the metal-containing nanoparticles 140 which are deposited in a thickness of 13 nm, 15 nm, 19 nm, respectively.

It may be noted that the metal-containing nanoparticles 140 are formed in a 3-D semi sphere shape due to low wetting between the alumina insulating film 130 and Ag which grows thereon. It is determined by the SEM image that when Ag is deposited in a thickness of 19 nm in an embodiment, height of the semi sphere shaped Ag is 50 nm.

In another general aspect, there is provided a Raman scattering apparatus including any one substrate for surface enhanced Raman scattering among the substrates described above. The Raman scattering apparatus may include a light source, a substrate for surface enhanced Raman scattering, and a detector configured to detect Raman scattering, wherein the substrate for surface enhanced Raman scattering may include one substrate for surface enhanced Raman scattering among the substrates described above. Detailed description about the light source and the detector may be omitted since they may be ones known in the art.

Figure 5:
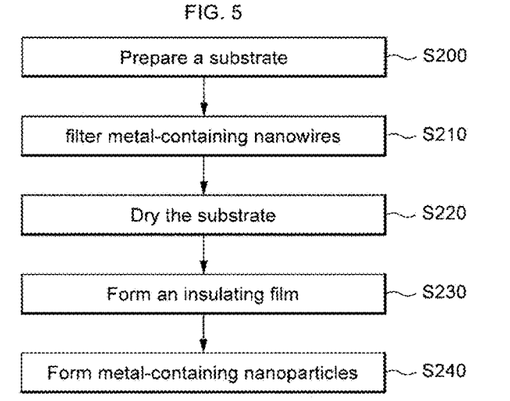
FIG. 5 is a block view illustrating an example of a method for fabricating a substrate for surface enhanced Raman scattering.

FIG. 5 is a block view illustrating an example of a method for fabricating a substrate for surface enhanced Raman scattering.

Referring to FIG. 5, in S200, a substrate 110 may be prepared. The substrate 110 may include a plurality of pores.

In S210, a solution 120 including metal-containing nanowires 122 may be filtered to aggregate the metal-containing nanowires 122 on the substrate 110.

A vacuum filtration may be used in an embodiment of the present disclosure.

A thickness of the metal-containing nanowires 122 to be aggregated may be adjusted by utilizing a concentration of the metal-containing nanowires 122 in the solution 120 and filtration volume of the solution 120.

A density of the metal-containing nanowires 122 to be aggregated may be adjusted by utilizing a concentration of the metal-containing nanowires 122 in the solution 120 and filtration volume of the solution 120.

In S220, the substrate 110, on which the metal-containing nanowires 122 are aggregated, may be dried.

When the substrate 110 is dried, materials which are not filtered off and remained, except the metal-containing nanowires 122, may be removed. Heat treatment may be used to accelerate drying. In an embodiment of the present disclosure, the substrate 110 may be placed on a hot plate heated to 150° C. to 170° C. to dry within 5 minutes.

In S220, a substrate for surface enhanced Raman scattering may be fabricated. However, the steps of from S230 to S240 may be further performed to obtain enhanced Raman signals.

In S230, an insulating film 130 may be formed on the metal-containing nanowires 122.

The insulating film 140 may be formed by using any one of vacuum deposition and solution processing, but it is not limited thereto.

The vacuum deposition may be any one chosen from atomic layer deposition, chemical vapor deposition, sputtering and thermal vapor deposition, but it is not limited thereto.

The solution processing may be any one chosen from spin coating, dip coating and dropping.

In an embodiment of the present disclosure, the thermal vapor deposition is used.

In S240, the metal-containing nanoparticles 140 may be formed. The metal-containing nanoparticles 140 may be formed by vacuum depositing a metal. The vacuum deposition may be one chosen from sputtering, evaporation and chemical vapor deposition, but it is not limited thereto.

Thickness or density of the metal-containing nanoparticles 140 may be adjusted by controlling deposition conditions such as a deposition time and the like during deposition process.

Figure 6:
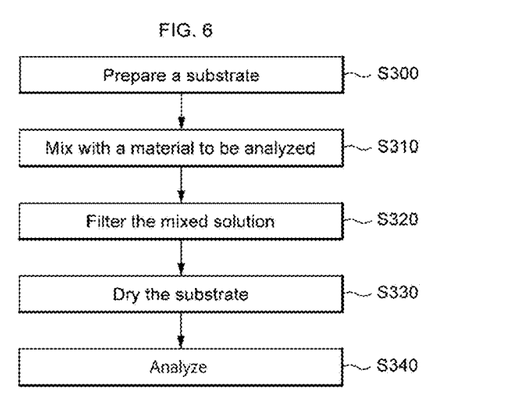
FIG. 6 is a block view illustrating an example of an analyzing method using a substrate for surface enhanced Raman scattering.

FIG. 6 is a block view illustrating an example of an analyzing method using a substrate for surface enhanced Raman scattering.

Referring to FIG. 6, in S300, a substrate 110 may be prepared. Materials and properties of the substrate 110 are the same as described above.

In S310, a material to be analyzed may be added to a solution 120 including metal-containing nanowires 122. Kinds, sizes and properties of the metal-containing nanowires 122 are the same as described above. As described above, a coating material such as polyvinylpyrrolidone (PVP) may be mixed to the solution 120 to ensure dispersion stability of the metal-containing nanowires 122. The coating material may be removed using heat treatment or may be used to control nanogaps.

In S320, the mixed solution 120 may be filtered. Vacuum filtration is used in an embodiment of the present disclosure. When the mixed solution 120 is filtered, the material to be analyzed may be positioned on the nanogaps between metal-containing nanowires 122 naturally without any separate process. For example, the material to be analyzed may be placed at hot spots to efficiently provide enhanced Raman signal during analyzing the Raman signals.

In S330, the substrate 110 may be dried. During drying the substrate 110, materials, except the material to be analyzed and the metal-containing nanowires 122 which are not filtered through and thus remained, may be removed. According to an embodiment, the coating material present on the surface of the metal-containing nanowires 122 may be remained to control nanogaps.

In S340, Raman signals of the material to be analyzed may be detected using laser irradiation to the substrate 110. As described above, the material to be analyzed may be also present between the nanogaps to provide enhanced Raman signals.

Figure 7:
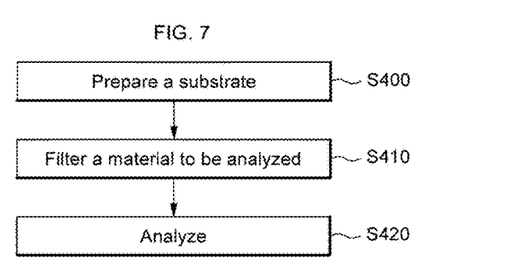
FIG. 7 is a block view illustrating an example of an analyzing method using a substrate for surface enhanced Raman scattering.

FIG. 7 is a block view illustrating an example of an analyzing method using a substrate for surface enhanced Raman scattering.

Referring to FIG. 7, in S400, a substrate for surface enhanced Raman scattering having above described structural properties may be prepared. The substrate for surface enhanced Raman scattering may be prepared by utilizing the method described above.

In S410, the material to be analyzed may be filtered. The material to be analyzed may be adsorbed to one area among various nanogaps during the filtration.

In S420, Raman signals of the material to be analyzed may be detected using laser irradiation to the substrate 110. As described above, the material to be analyzed may be also present between the nanogaps to provide enhanced Raman signals.

Figure 8:
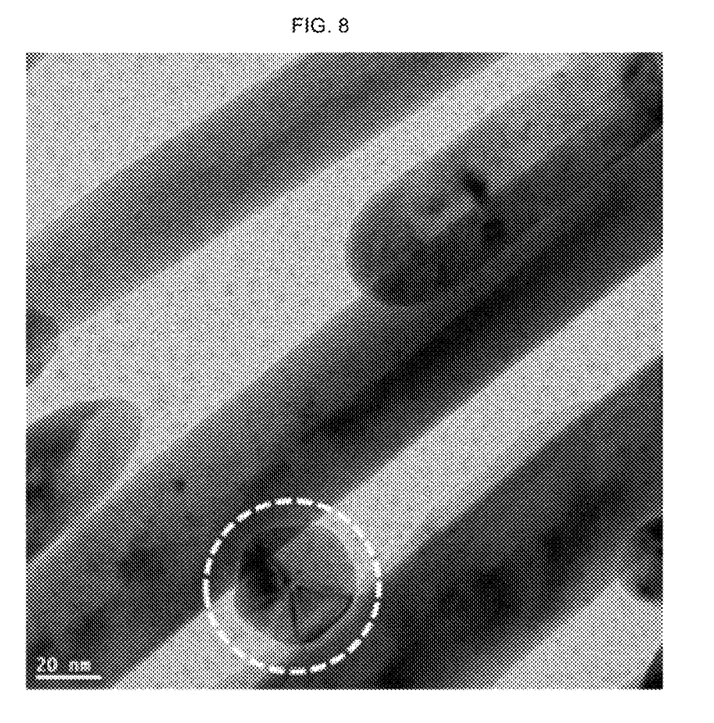
FIG. 8 is a transmission electron microscope image of an example of metal-containing nanowires.

FIG. 8 is a transmission electron microscope image of an example of metal-containing nanowires.

Referring to FIG. 8, cross points (circular dotted line), which are formed when the metal-containing nanowires 122 are crossed each other, may be clearly provided.

Figure 9:
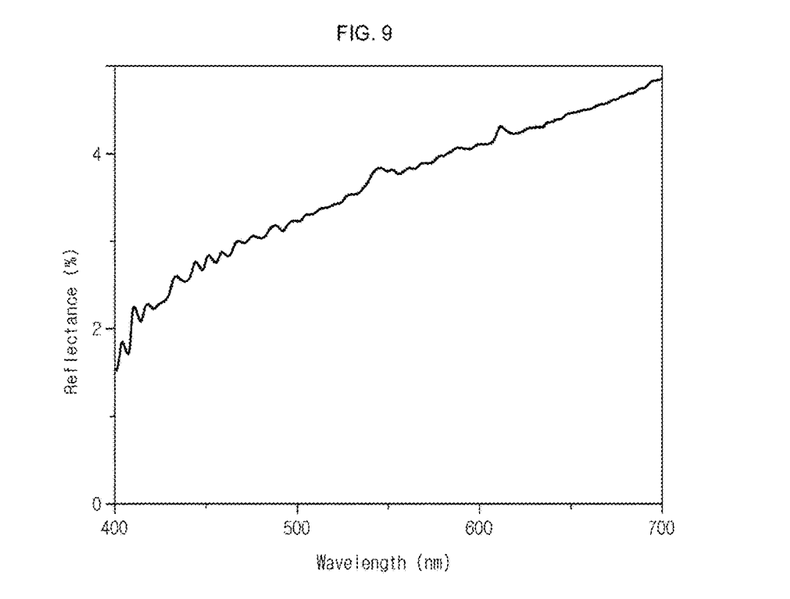
FIG. 9 is a reflectance graph of an example of a substrate for surface enhanced Raman scattering.

FIG. 9 is a reflectance graph of an example of a substrate for surface enhanced Raman scattering.

The substrate for surface enhanced Raman scattering in FIG. 9 only includes a substrate 110 and metal-containing nanowires 122.

The substrate 110 used in FIG. 9 is a glass fiber filter with a thickness of 0.7 µm. The metal-containing nanowires 122 in the solution 110 have a diameter of about 40 nm and a length of abut 50 µm and Ag is used. Vacuum filtration is used to aggregate the metal-containing nanowires 122 on the substrate 110.

The substrate for surface enhanced Raman scattering of the present disclosure has excellent optical properties including less than 5% of reflectance at a wavelength range of 400-700 nm which is a visible range. Such a low reflectance is due to effective light absorption through numerous different nanogaps between Ag nanowires 122.

Figure 10:
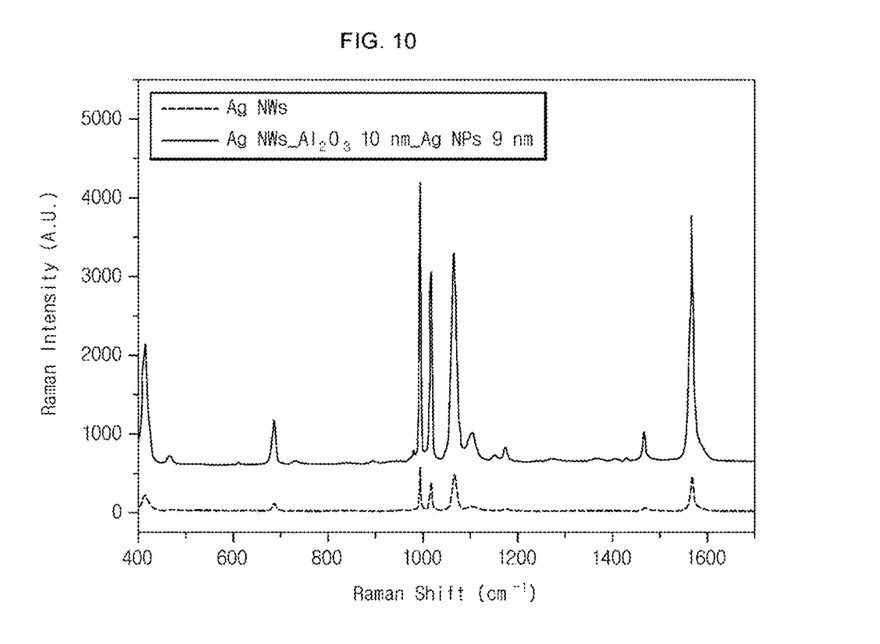
FIG. 10 is a graph comparing Raman signals using an example of a substrate for surface enhanced Raman scattering.

FIG. 10 is a graph comparing Raman intensities using an example of a substrate for surface enhanced Raman scattering.

Referring to FIG. 10, Raman intensities were compared using the substrate for surface enhanced Raman scattering, which was prepared at the same conditions described in FIG. 9, and the substrate for surface enhanced Raman scattering, which was prepared by further including the insulating film 130 of 10 nm of alumina ($Al_2O_3$) and the metal-containing nanoparticles 140 of 9 nm of Ag on the substrate for surface enhanced Raman scattering of FIG. 9.

The former was represented by Ag NWs, while the latter was represented by Ag NWs_$Al_2O_3$ 10 nm_Ag NPs 9 nm.

Both substrates were immersed in 2 mM of a benzenethiol (BT) solution for about 1 hour and then rinsed with ethanol so that benzenethiol molecules were adsorbed on the substrate 110 in a single layer. Raman intensity of the both substrates for surface enhanced Raman scattering were determined using Raman spectroscopy. Wavelength and intensity of incident laser were 632.8 nm and 0.4 mW, respectively. Ag NWs_Al2O3 10 nm_Ag NPs 9 nm showed 5 times or more of Raman intensity compared to Ag NWs.

EXAMPLE 1

Excitation laser wavelength): 632.8 nm
Objective lens: 50×
Spot size: 2 µm
Power: 0.4 mW While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

DESCRIPTION OF REFERENCE NUMERALS

110: Substrate
120: Solution
122: Metal-containing nanowire
124: Filtrate
130: Insulator
140: Metal-containing nanoparticles

What is claimed is:

1. A substrate for surface enhanced Raman scattering comprising:
    a filter substrate comprising a plurality of pores; and
    metal-containing nanowires configured not to pass through the pores but to be stacked on the substrate, wherein the metal-containing nanowires form nanogaps configured to induce surface plasmon resonance with adjacent metal-containing nanowires, wherein each metal-containing nanowire is stacked in irregular directions on the filter substrate to form a plurality of cross points, wherein hot spots at which plasmon resonance occurs are formed near the cross points, wherein a coating material is present on the surface of the metal-containing nanowires and the nanogaps are adjusted using the coating material, and wherein each metal-containing nanowire is stacked in a pre-determined thickness or above, and the pre-determined thickness is determined based on a thickness where increase in the Raman intensity of the substrate for surface enhanced Raman scattering becomes saturated.

2. The substrate for surface enhanced Raman scattering of claim 1, further comprising:
an insulating film formed on the metal-containing nanowires; and
metal-containing nanoparticles formed on the insulating film and configured to form nanogaps inducing plasmon resonance by being spaced apart from each other.

3. The substrate for surface enhanced Raman scattering of claim 2, wherein the nanogaps inducing surface plasmon resonance are formed between the metal-containing nanoparticles and the metal-containing nanowires.

4. The substrate for surface enhanced Raman scattering of claim 1, wherein the substrate is selected one from the group consisting of glass fiber, alumina, Teflon (polytetrafluoroethylene, PTFE), polycarbonate (PC), cellulose and paper.

5. The substrate for surface enhanced Raman scattering of claim 1, wherein the metal-containing nanowires is formed on the substrate by filtering a solution including metal-containing nanowires through the substrate to be stacked on the substrate using vacuum filtration.

6. The substrate for surface enhanced Raman scattering of claim 1, wherein the metal is selected from the group consisting of Ag, Al, Au, Co, Cu, Fe, Li, Ni, Pd, Pt, Rh, Ru and an alloy thereof.

7. The substrate for surface enhanced Raman scattering of claim 1, wherein the substrate is dried using heat treatment to eliminate materials, except the metal-containing nanowire, remaining on the substrate.

8. The substrate for surface enhanced Raman scattering of claim 1, wherein a thickness of the metal-containing nanowires to be stacked is adjusted using a concentration of the metal-containing nanowires in the solution and a filtration volume of a solution.

9. The substrate for surface enhanced Raman scattering of claim 5, wherein a density of the metal-containing nanowires to be stacked is adjusted using a concentration of the metal-containing nanowires in the solution and a filtration volume of the solution.

10. The substrate for surface enhanced Raman scattering of claim 5, wherein a wavelength of the surface plasmon resonance is adjusted using at least one selected from the group consisting of a material, a diameter, and a length of the metal-containing nanowires.

11. The substrate for surface enhanced Raman scattering of claim 2, wherein the insulating film is one selected from the group consisting of alumina, metal oxide, metal sulfide, metal halide, silica, zirconium oxide and iron oxide.

12. The substrate for surface enhanced Raman scattering of claim 2, wherein the insulating film is formed using one selected from the group consisting of vacuum deposition and solution processing.

13. The substrate for surface enhanced Raman scattering of claim 2, wherein the metal-containing nanoparticles are formed through vacuum deposition with a Raman active material.

14. The substrate for surface enhanced Raman scattering of claim 13, wherein the vacuum deposition is performed using one selected from the group consisting of sputtering, evaporation and chemical vapor deposition.

15. A Raman scattering apparatus comprising the substrate for surface enhanced Raman scattering of claim 1.

16. A method for fabricating the substrate for surface enhanced Raman scattering, the method comprising:
preparing a filter substrate comprising a plurality of pores;
filtering a solution comprising metal-containing nanowires to stack the metal-containing nanowires in irregular directions on the filter substrate to form a plurality of cross points;
drying the filter substrate;
wherein the metal-containing nanowires do not pass through the pores and form nanogaps configured to induce surface plasmon resonance with adjacent metal-containing nanowires;
wherein hot spots at which plasmon resonance occurs are formed near the cross points;
wherein a coating material is present on the surface of the metal-containing nanowires and the nanogaps are adjusted using the coating material; and
wherein each metal-containing nanowire is stacked in a pre-determined thickness or above, and the pre-determined thickness is determined based on a thickness where increase in the Raman intensity of the substrate for surface enhanced Raman scattering becomes saturated.

17. An analyzing method using a substrate for surface enhanced Raman scattering comprising:
preparing a substrate for surface enhanced Raman scattering of claim 1;
filtrating a material to be analyzed to the substrate; and
detecting a Raman signal by light irradiation into the material to be analyzed.

* * * * *